United States Patent [19]

Beachy

[11] Patent Number: 5,143,721

[45] Date of Patent: Sep. 1, 1992

[54] METHOD OF SMOOTHING AND REDUCING FINGERNAIL CRACKING AND PEELING BY RUBBING OR BUFFING WITH DOLOMITE POWDER

[76] Inventor: Frances Beachy, P.O. Box 2049, Rancho Santa Fe, Calif. 92067

[21] Appl. No.: 729,625

[22] Filed: Jul. 15, 1991

[51] Int. Cl.$^5$ .......................... A01N 7/04; A01N 7/043
[52] U.S. Cl. ........................................ 424/61; 424/682; 424/686; 424/687
[58] Field of Search .................. 424/682, 686, 687, 61

[56] References Cited

U.S. PATENT DOCUMENTS 4,626,428  12/1986  Weisberg et al. ...................... 424/61
4,669,491  6/1987  Weisberg et al. ...................... 424/70

Primary Examiner—Allen J. Robinson
Assistant Examiner—John D. Pak
Attorney, Agent, or Firm—Frank D. Gilliam

[57] ABSTRACT

A method of reducing cracking and peeling of human fingernails and toenails and, apparently, of polishing and hardening and toughening them. A finely divided powder comprising substantially pure dolomite is provided. The powder is manually rubbed on the fingernails for periods on a regular schedule. After a short time, fingernails that had previously been subject to chipping and cracking are found to resist chipping and cracking and to appear to have a harder and tougher surface.

7 Claims, No Drawings

METHOD OF SMOOTHING AND REDUCING FINGERNAIL CRACKING AND PEELING BY RUBBING OR BUFFING WITH DOLOMITE POWDER

BACKGROUND OF THE INVENTION

This invention relates in general to the treatment of human finger and toe nails and, more specifically, to a method for reducing chipping, peeling and cracking which polishes and strengthens those nails.

Problems with fingernails chipping and cracking, often resulting in unattractive deep and often painful cracks, have long existed. This is a particular problem for women who often apply fingernail polish and often remove it using volatile solvents or those who work in an environment that treats fingernails roughly.

A number of different treatments have been proposed to harden finger and toe nails, such as the application of formaldehyde or other agents that appear to react with the proteins of the nails, which are basically keratinous proteins. While having some hardening effects, these materials also tend to make nails more brittle, resulting in increased cracking.

Other fingernail hardening treatments include the application of a mixture of lanolin, unsalted butter, beeswax, rosin, copper acetate and turpentine to which is added a small amount of a mixture of titanium dioxide, mineral oil and a fragrance, as disclosed by Rassarelli in U.S. Pat. No. 4,933,175. This composition seems to be primarily a surface lubricant, with the titanium dioxide adding a white color. Brown, in U.S. Pat. No. 4,631,186 proposes treating fingernails with sour cherry juice to strengthen them and enhance growth. Mayer, in U.S. Pat. No. 3,989,817 describes treating nails with an aqueous solution of walnut oil containing a small amount of potassium iodide in an inert, fatty, carrier.

All of these prior treatments seem to be simple surface coatings, although some chemical reaction could be present to somewhat harden the nails. Despite the large number of fingernail treating creams and lotions on the market, there continues to be a problem for a large number of persons of fingernail chipping, splitting and cracking. Such conditions can be both unsightly and painful.

SUMMARY OF THE INVENTION

The above-noted problems, and others, are overcome by a method of treating finger and toe nails which comprises rubbing the nails with a composition consisting essentially of finely divided dolomite powder.

While the powder is preferably essentially pure dolomite, minor additives such as fragrances, colorants or the like may be added if desired.

DETAILED DESCRIPTION OF PREFERRED EMBODIMENTS

Dolomite is a naturally occurring mineral, having the composition $CaMg(CO_3)_2$. It has a mohs hardness of about 3.5 to 4 and a specific gravity of about 2.8 to 2.9. Dolomite is often found in substantially pure natural deposits of the mineral dolomite or dolomite rock, generally white in color although other colors occur. For the purposes of the method of this invention, the dolomite should be substantially pure, although impurities, such as small amounts of calcite, that are not harder than dolomite are acceptable. Hard impurities, such as quartz, are to be avoided.

Prior art uses of dolomite have been primarily in the manufacture of magnesia for use in cement, refractories and the like or for medical purposes, to be taken internally as an antacid or mild laxatives. Dolomite has been used as a "health food" additive, primarily as an antacid.

Although more expensive, the dolomite composition, calcium magnesium carbonate, can be manufactured in a very pure state by conventional chemical methods. For best results, substantially equal atomic percentages of calcium and magnesium are preferred.

In the performance of the method of this invention, finely divided dolomite is provided in the form of a fine, dry powder. The powder should be sufficiently fine to feel soft when rubbed between the fingertips. A small amount of the dolomite powder is periodically rubbed on each finger or toe nail. The powder may be rubbed with a fingertip or a small soft pad. Excellent results are obtained when the powder is rubbed or buffed on each nail for about one half minute about two times each day, although significant benefits are derived from fewer or shorter applications.

Tests with a number of persons having problems with nails cracking have shown significant reductions in cracking and chipping after a few week's use of this dolomite powder. While the mechanism by which this powder reduces cracking and chipping is not fully understood, it is theorized that the polishing action of the relatively soft but slightly abrasive dolomite powder very lightly abrades and polishes the nail surface, eliminating microscopic cracks and fissures which would otherwise develop into cracks or chips. Softer powders would not cause this abrasion and polishing effect, while harder powders, such as quartz powders, would cause scratches that would initiate even more cracks and chips. Of course, other mechanisms and possible chemical interactions cannot be ruled out. Empirical tests have shown the significant advantages of this treatment in reducing cracks and chips.

Any suitable dolomite powder may be used in the practice of the method of this invention. The dolomite may be mined, crushed and ground from naturally occurring relatively pure deposits of dolomite, or the composition can be manufactured, as desired. A preferred powder for use in this method is available from Schff Products, Inc., Moonachie, New Jersey, under the designation: "Natural Dolomite Powder". While that powder is marketed as a health food additive, to be taken internally, it has been found to be excellent for the purposes of this invention.

If desired, minor quantities of various additives such as fragrances or dyes to color the powder may be added. Preferably, the dolomite powder is used alone, since it is non-toxic and non-allergenic. Other applications, variations and ramifications of this invention will occur to those skilled in the art upon reading this disclosure. Those are intended to be included within the scope of this invention, as defined in the appended claims.

I claim:

1. The method of reducing cracking and chipping of fingernails and toenails which comprises the steps of:
   providing a finely divided powder consisting essentially of dolomite; and
   rubbing fingernails and/or toenails with an effective amount of said powder;

whereby cracking and chipping of those nails is reduced.

2. The method according to claim 1 where the powder is rubbed on each nail for at least about one half minute at least about two times each day.

3. The method according to claim 1 wherein said dolomite powder is substantially free from materials hving hardnesses greater than that of dolomite.

4. The method according to claim 1 where said dolomite powder is derived from naturally occurring dolomite rock which is substantially free from materials harder than dolomite.

5. The method according to claim 1 where said dolomite powder consists of calcium magnesium carbonate prepared by chemical synthesis methods.

6. The method of reducing cracking and chipping of fingernails and toenails which comprises the steps of:
   providing a finely divided powder consisting essentially of dolomite;
   said powder being substantially free from materials having hardnesses greater than that of dolomite;
   said powder being derived from naturally occurring dolomite rock; and
   rubbing fingernails and/or toenails with said powder.

7. The method according to claim 6 where the powder is rubbed on each nail for at least about one half minute at least about two times each day.

* * * * *